United States Patent [19]

Tjerneld et al.

[11] Patent Number: 4,740,304
[45] Date of Patent: Apr. 26, 1988

[54] COMPOSITION FOR USE IN A TWOPHASE OR MULTIPHASE SYSTEM

[75] Inventors: Folke G. Tjerneld, Lund; Göte O. Johansson, Arlöv, both of Sweden

[73] Assignee: Perstorp AB, Pestrop, Sweden

[21] Appl. No.: 893,864

[22] Filed: Aug. 6, 1986

[30] Foreign Application Priority Data

Aug. 8, 1985 [SE] Sweden ................................ 8503742

[51] Int. Cl.$^4$ ................................................ B01D 11/04
[52] U.S. Cl. ........................................ 210/639; 210/647
[58] Field of Search ............... 106/210; 210/634, 639, 210/645, 647; 536/111; 524/50

[56] References Cited

U.S. PATENT DOCUMENTS 3,077,054  2/1963  Niemeijer et al. .................. 524/50
4,361,669  11/1982  Evans et al. ...................... 524/50

FOREIGN PATENT DOCUMENTS 1067692  5/1967  United Kingdom .
1395777  5/1975  United Kingdom .
1433732  4/1976  United Kingdom .
1565917  1/1977  United Kingdom .
1551807  4/1977  United Kingdom .
1514720  6/1978  United Kingdom .
1584921  2/1981  United Kingdom .
2046772  5/1983  United Kingdom .
2117782  10/1983  United Kingdom .

Primary Examiner—Frank Sever
Attorney, Agent, or Firm—Stevens, Davis, Miller & Mosher

[57] ABSTRACT

Composition for use in a twophase or a multiphase system for extraction, purification, concentration and/or separation of biological substances. The composition is characterized in that it contains hydroxyalkyl starch with a degree of substitution in respect of hydroxyalkyl groups of more than 0.02 per glucose unit on an average and with an average molecular weight lower than 800000, preferably at most 400000 and most preferably at most 250000.

5 Claims, 10 Drawing Sheets

PHASE DIAGRAM PEG 8000-HPS

PHASE DIAGRAM PEG 8000-HPS

THE INFLUENCE OF POLYMER BONDED LIGANDS ON THE DISTRIBUTION OF GLUCOSE-6-PHOSPHATE-DEHYDROGENASE. (▲) NO ADDITION OF PROCION YELLOW-HPS AND (•) 3% PROCION YELLOW-HPS OF TOTAL CONTENT OF HPS.

THE SOLUBILITY OF GAMMAGLOBULINE IN SOLUTIONS OF DIFFERENT BOTTOM PHASE POLYMERS. (■) DEXTRAN 500, (▲) HPS WITH $M_w = 125000$ AND (●) HPS WITH $M_w > 800000$.

THE ENZYME ACTIVITY AS A FUNCTION OF THE BEAKER NUMBER.
THE TWOPHASE SYSTEM PEG 8000-HPS. 5% CIBACRON BLUE-PEG ADDED.

COUNTERCURRENT DISTRIBUTION OF A MIXTURE OF DNA AND RNA USING A TWOPHASE SYSTEM.

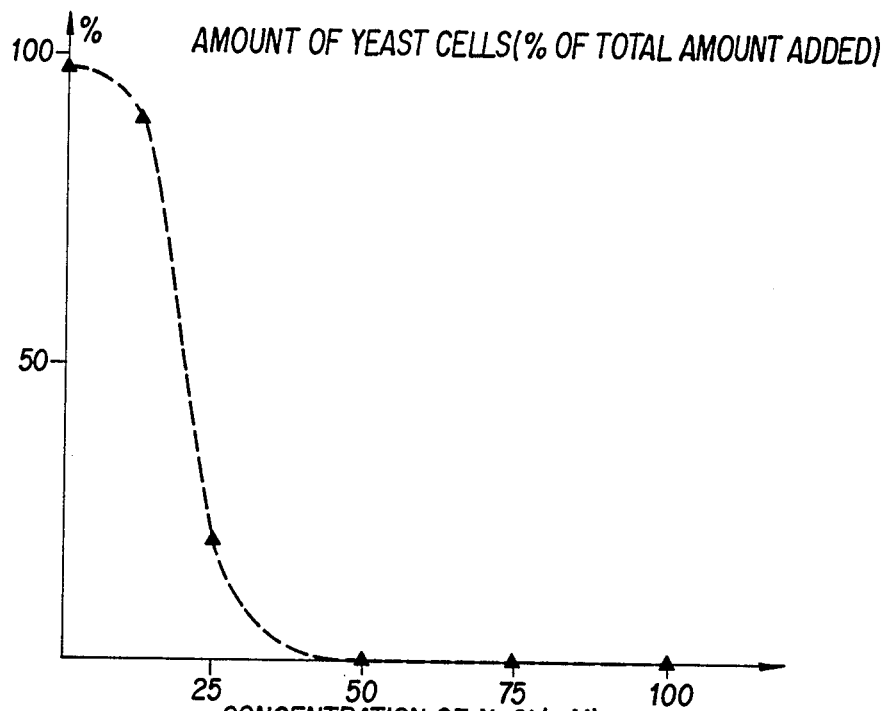
FIG. 6a: AMOUNT YEAST CELLS IN TOPPHASE, % OF TOTAL ADDED
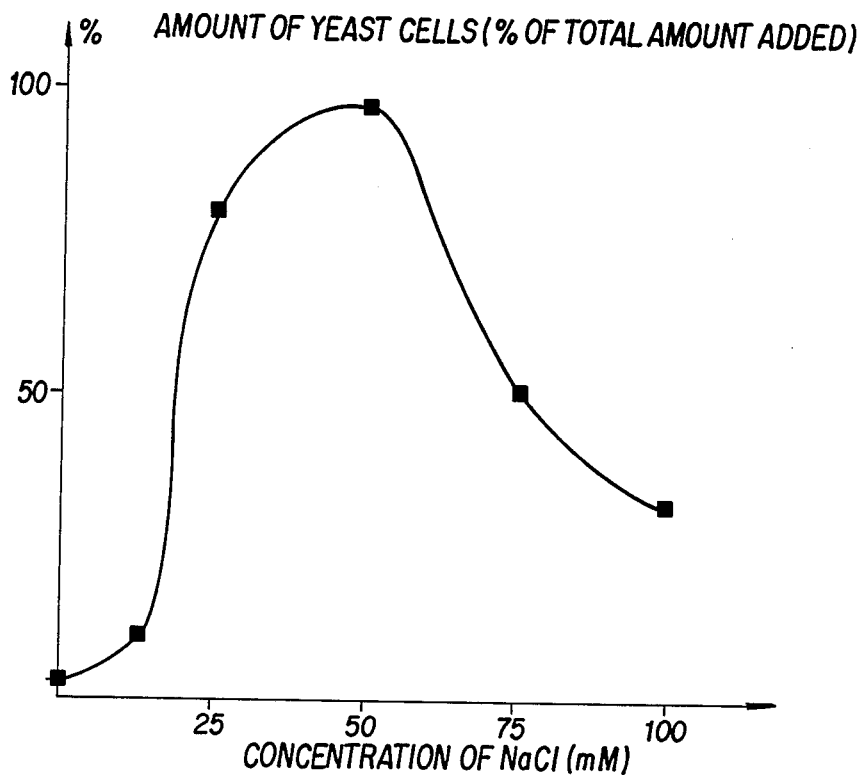
FIG. 6b: AMOUNT YEAST CELLS IN INTERFACE, % OF TOTAL ADDED

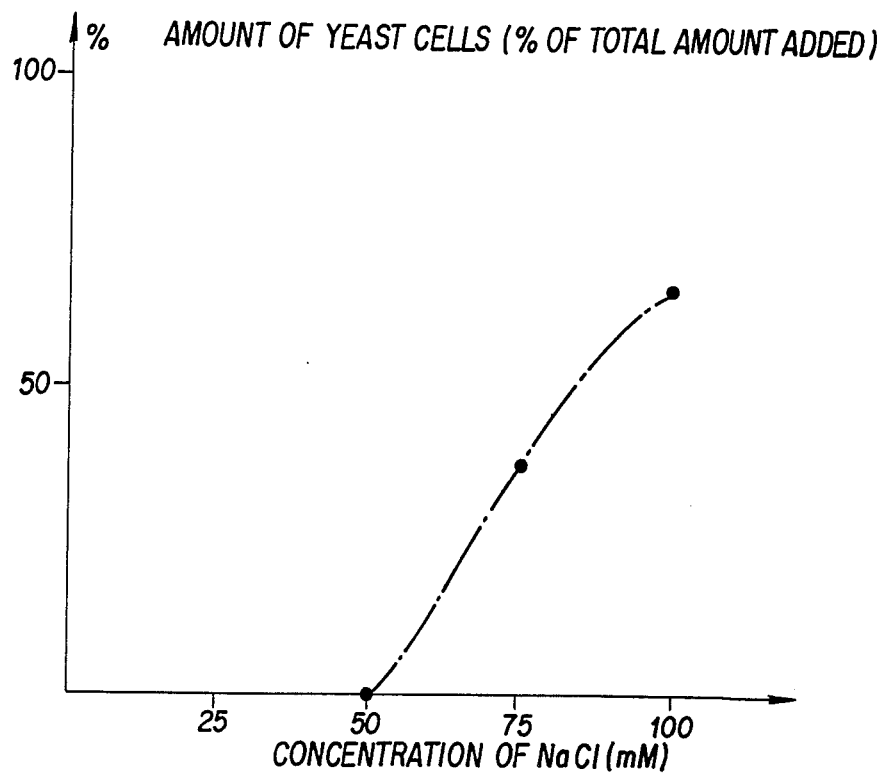
FIG. 6c: AMOUNT OF YEAST CELLS IN BOTTOMPHASE, % OF TOTAL ADDED
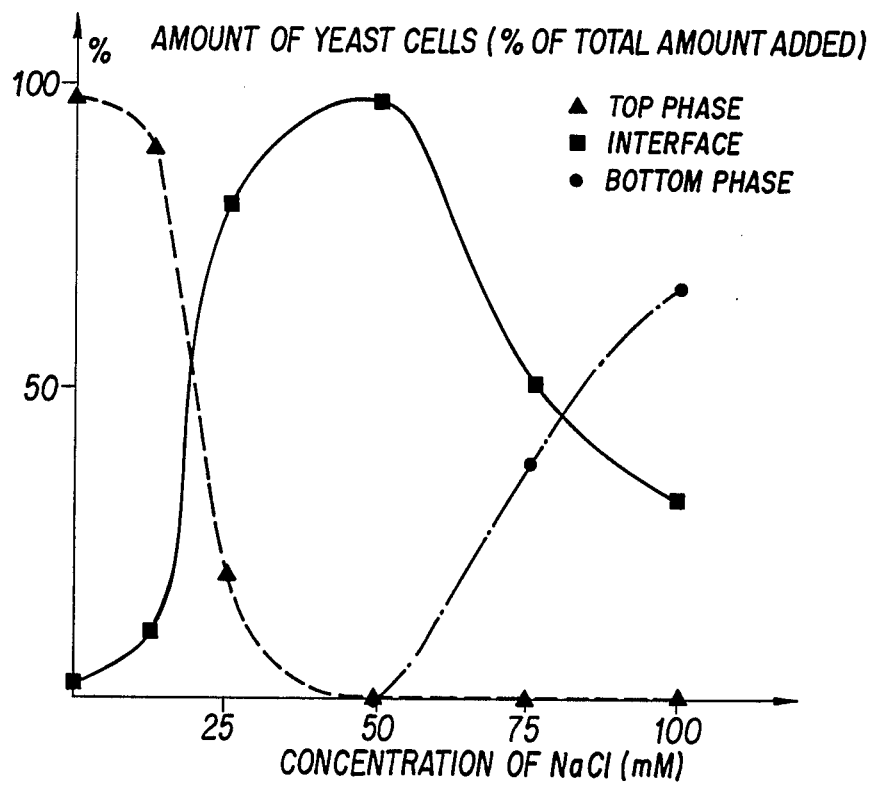
FIG. 6d: SUMMARY OF FIGURE 6a-c

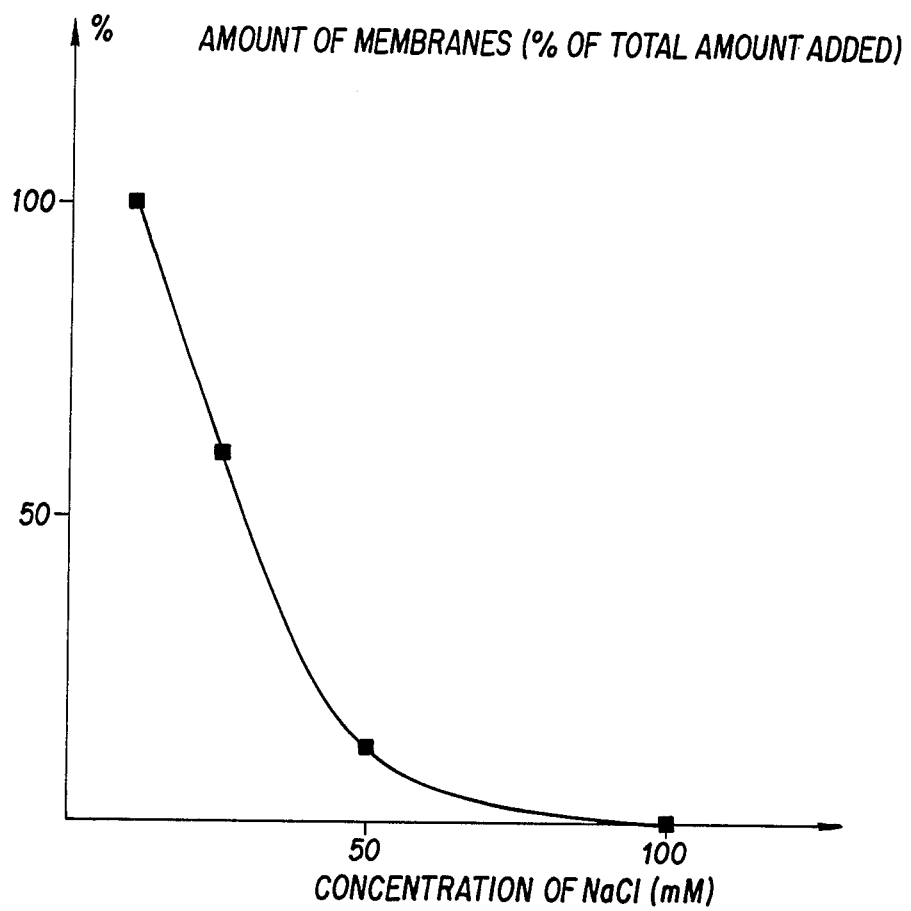
FIG. 7: AMOUNT OF SYNAPTIC MEMBRANES IN TOPPHASE, % OF TOTAL ADDED.

COMPOSITION FOR USE IN A TWOPHASE OR MULTIPHASE SYSTEM

The present invention relates to a composition for use in a twophase or multiphase system for extraction, purification, concentration and/or separation of biological substances.

Twophase or multiphase systems are disclosed in Partition of Cell Particles and Macromolecules NY (1971) by professor Per-Åke Albertsson. Said systems were intended to make it possible to bring about liquid-liquid extraction of biological macromolecules, for example proteins and nucleic acids and particles, for example cell membranes, cell organelles, cells and virus.

Said systems were obtained by mixing aqueous solutions of two or more polymeric substances. The different polymer solutions were enriched in one phase each. The composition and volumes of the phases depend on the kind and molecular weight of the polymers, the concentration of the polymers and the temperature.

The properties, which are unique for these systems and make them useful for extraction, purification, concentration and/or separation of biological materials, are the very high water content of the liquid phases, often 85–99 percent and the possibility to process soluble as well as particle formed substances.

The systems which previously turned out to have the most advantageous properties in respect of separation times and distribution of biological material between the polymer phases consisted of the polymers dextran and polyethylene glycol (PEG). The dextran polymer was so expensive that a technical use in a twophase system was impossible from an economic point of view. Moreover, the dextran also caused a rather high viscosity in the dextran containing phase. This resulted in a prolonged processing time.

Albertsson tested a number of twophase polymer systems based on other water soluble polymers than PEG and dextran. These other polymer systems had several disadvantages such as poor stability, bad partition properties or high viscosity with accompanying unreasonably long separation times.

The demand on a polymer which should replace dextran in above-mentioned systems when they are to be used for processing of biological substances on a large scale, is that the price of the polymer is low enough, that the viscosity is low and that the partition properties of the system formed are as good as or better than in systems containing dextran.

Quite surprisingly it has now been possible according to the present invention to satisfy the above desire and bring about a composition for use in a twophase or a multiphase system for extraction, purification, concentration and/or separation of biological substances. The composition is characterized in that it contains hydroxyalkyl starch with a degree of substitution in respect of hydroxyalkyl groups of more than 0.02 per glucose unit on an average and with an average molecular weight lower than 800000.

Preferably the average molecular weight of the hydroxyalkyl starch is higher than 5000 and at most 400000. Most preferably it is at most 250000.

A lower degree of substitution than 0.02 hydroxyalkyl groups per glucose unit on an average gives polymer solutions with a poor stability, i.e. formation of a gel.

As mentioned the molecular weight of the hydroxyalkyl starch should most preferably amount to at most 250000. Then a twophase system with better properties concerning distribution of the biological substances between the phases of the system is obtained. Furthermore, at a low molecular weight of the hydroxyalkyl starch it is for instance possible to process a larger amount of proteins per volume of polymer dissolved in water than at a high molecular weight.

The use of hydroxyalkyl starch according to the invention gives a system with a viscosity being low enough for technical use. The polymer solutions also get a good stability.

The composition according to the invention preferably contains hydroxypropyl starch (HPS).

In addition the composition according to the invention usually contains also at least one polymer selected from the group consisting of polyethylene glycol, polypropylene glycol, methoxypolyethylene glycol, polyvinyl alcohol, polyvinyl pyrrolidone, methyl cellulose, ethylhydroxyethyl cellulose, hydroxyethyl cellulose and Ficoll.

At the use of the composition according to the invention the hydroxyalkyl starch and the additional polymer or polymers are suitably dissolved in water.

Often the hydroxyalkyl starch and the other polymers constitute 1–40 percent of the aqueous solution.

Then the biological material which is to be processed is added, whereupon stirring takes place.

When the stirring has been stopped, distinctly limited liquid layers (phases) are formed. The different components of the biological material are partitioning between the layers.

Finally, the different components are recovered from the specific phases. Possibly the components can then be purified further in a suitable way.

According to one embodiment of the invention it is possible to get a more selective distribution of the components of the biological material between the different phases. Then a so-called affinity partition can be used, whereby at least one substituted ligand is added to the polymer solution.

The ligands used can consist of charged as well as uncharged groups. As examples of positively charged ligands, trimethylamino groups, diethylaminoethyl groups and quarternary aminoethyl groups can be mentioned.

Negatively charged ligands can for example consist of carboxylic groups, sulphonate groups, carboxymethyl groups, carboxyethyl groups, sulphate groups and phosphate groups.

Further examples of suitable ligands are fatty acids or derivatives of fatty acids, triazin dyestuffs such as Cibacron Blue and Procion Yellow, lectins, coenzymes, analogues of adenosine triphosphate, adenosine diphosphate and adenosine monophosphate, thiamine binding proteins, glucoproteins, flavin binding proteins and biotin binding proteins.

To obtain an affinity partition, the above ligands can be bonded to at least one polymer in the twophase system, i.e. hydroxyalkyl starch and/or a polymer selected from the group consisting of polyethylene glycol, polypropylene glycol, methoxypolyethylene glycol, polyvinyl alcohol, polyvinyl pyrrolidone, methyl cellulose, hydroxyethyl cellulose, ethylhydroxyethyl cellulose and Ficoll.

Usually, the ligand and the polymer are bonded together by covalent bonds.

The advantages obtained at the use of ligands is that they selectively bind certain components of the biological material. Then a larger proportion of the specific compound will get into a certain phase, whereby of course the yield will get higher.

Another way of directing the distribution of the biological components between the phases is to add a water soluble salt to the polymer solution. Said distribution is also influenced by the molecular weight of the polymers present.

The present invention will be further explained in connection with the embodiment examples below and the enclosed figures and tables. Thereby, examples 1–9, 18–22, 24–26, 28, 29 and 31–47 illustrate the invention, while the rest of the examples relate to comparison tests outside the scope of the invention.

BRIEF DESCRIPTION OF FIGURES

FIGS. 6a–6d show yeast cell distributions.

FIG. 7 shows amount of synaptic membranes in to-phase.

EXAMPLE 1

In a beaker hydroxypropyl starch with a degree of substitution in respect of hydroxypropyl groups of 0.14 per glucose unit on an average and with an average molecular weight of 125000 was dissolved in water together with polyethylene glycol with an average molecular weight of 8000.

Figure 1:
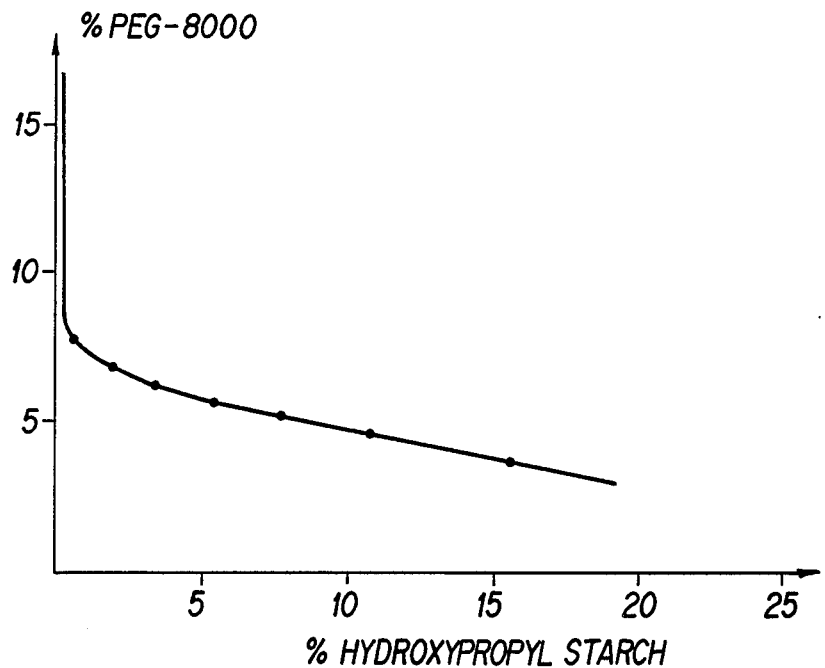
FIG. 1 shows a phase diagram PEG 8000-HPS.

The proportions between the hydroxypropyl starch and the polyethylene glycol were varied at a constant amount of water. The mixtures obtained were stirred for a short time, whereupon the stirring was stopped. Thereafter, it was established whether two phases had been obtained or not. The result is shown in FIG. 1. in the form of a so-called phase diagram.

EXAMPLE 2

0.7 g hydroxypropyl starch with a degree of substitution in respect of hydroxypropyl groups of 0.14 per glucose unit on an average and with an average molecular weight of 125000 was dissolved in water together with 0.25 g polyethylene glycol with an average molecular weight of 8000.

Sodium phosphate was added to the polymer solution obtained until a concentration of 10 m M was obtained. The total amount of twophase system was 5 g. 96 units of the enzyme β-galactosidase was added at stirring. The stirring was continued for a short while.

When the stirring was stopped, the solution formed two phases. Thereafter the amount of enzyme in the two phases was measured, whereby a measure on the distribution between the phases was calculated. The result is shown in Table 1.

EXAMPLE 3

The process according to Example 2 was repeated with the difference that a polyethylene glycol with an average molecular weight of 20000 was used. The result is shown in Table 1.

EXAMPLE 4

The process according to Example 2 was repeated with the difference that sodium chloride was added to a concentration of 0.1M. The result is shown in Table 1.

EXAMPLE 5

The process according to Example 3 was repeated with the difference that sodium chloride was added to a concentration of 0.1M. The result is shown in Table 1.

EXAMPLE 6

The process according to Example 2 was repeated with the difference that the enzyme was catalase instead. The result is shown in Table 1.

EXAMPLE 7

The process according to Example 3 was repeated with the difference that the enzyme was catalase. The result is shown in Table 1.

EXAMPLE 8

The process according to Example 4 was repeated with the difference that the enzyme was catalase instead. The result is shown in Table 1.

EXAMPLE 9

The process according to Example 5 was repeated with the difference that the enzyme was catalase instead. The result is shown in Table 1.

EXAMPLE 10

The process according to Example 2 was repeated with the difference that dextran with an average molecular weight of 500000 was used instead of the hydroxypropyl starch. The result is shown in Table 1.

EXAMPLE 11

The process according to Example 3 was repeated with the difference that dextran with an average molecular weight of 500000 was used instead of the hydroxypropyl starch. The result is shown in Table 1.

EXAMPLE 12

The process according to Example 4 was repeated with the difference that dextran with an average molecular weight of 500000 was used instead of the hydroxypropyl starch. The result is shown in Table 1.

EXAMPLE 13

The process according to Example 5 was repeated with the difference that dextran with an average molecular weight of 500000 was used instead of hydroxypropyl starch.

EXAMPLE 14

The process according to Example 6 was repeated with the difference that dextran with an average molecular weight of 500000 was used instead of the hydroxypropyl starch. The result is shown in Table 1.

EXAMPLE 15

The process according to Example 7 was repeated with the difference that dextran with an average molecular weight of 500000 was used instead of the hydroxypropyl starch. The result is shown in Table 1.

EXAMPLE 16

The process according to Example 8 was repeated with the difference that dextran with an average molecular weight of 500000 was used instead of the hydroxypropyl starch. The result is shown in Table 1.

EXAMPLE 17

The process according to Example 9 was repeated with the difference that dextran with an average molecular weight of 500000 was used instead of hydroxypropyl starch.

The result is shown in Table 1 from which it is evident that more than 60% of the enzyme is found in the polyethylene glycol phase at the processes according to Examples 2, 6, 10 and 14. In Example 2 more than 95% of the enzyme is found in the polyethylene glycol phase.

It is also evident from Table 1 that more than 85% of the enzyme is found in the bottom phase (hydroxypropyl starch and dextran respectively) at the processes according to Examples 5, 9, 13 and 17.

Thus, the result shows that hydroxypropyl starch—polyethylene glycol makes a twophase system which is as effective as dextran—polyethylene glycol.

EXAMPLE 18

0.025 g hydroxypropyl starch with an average molecular weight of 800000 and with a degree of substitution in respect of hydroxypropyl groups of 0.14 per glucose unit was dissolved in 1 ml of water.

3.75 mg gammaglobuline from rabbit was added to the polymer solution at stirring.

90% of the gammaglobuline was found in the starch solution.

The experiment was continued by addition of an increasing amount of hydroxypropyl starch. Then the precipitation of the gammaglobuline increased at an increasing content of hydroxypropyl starch, which is shown in FIG. 2.

EXAMPLE 19

The process according to Example 18 was repeated with the difference that hydroxypropyl starch with an average molecular weight of 125000 was used.

Figure 2:
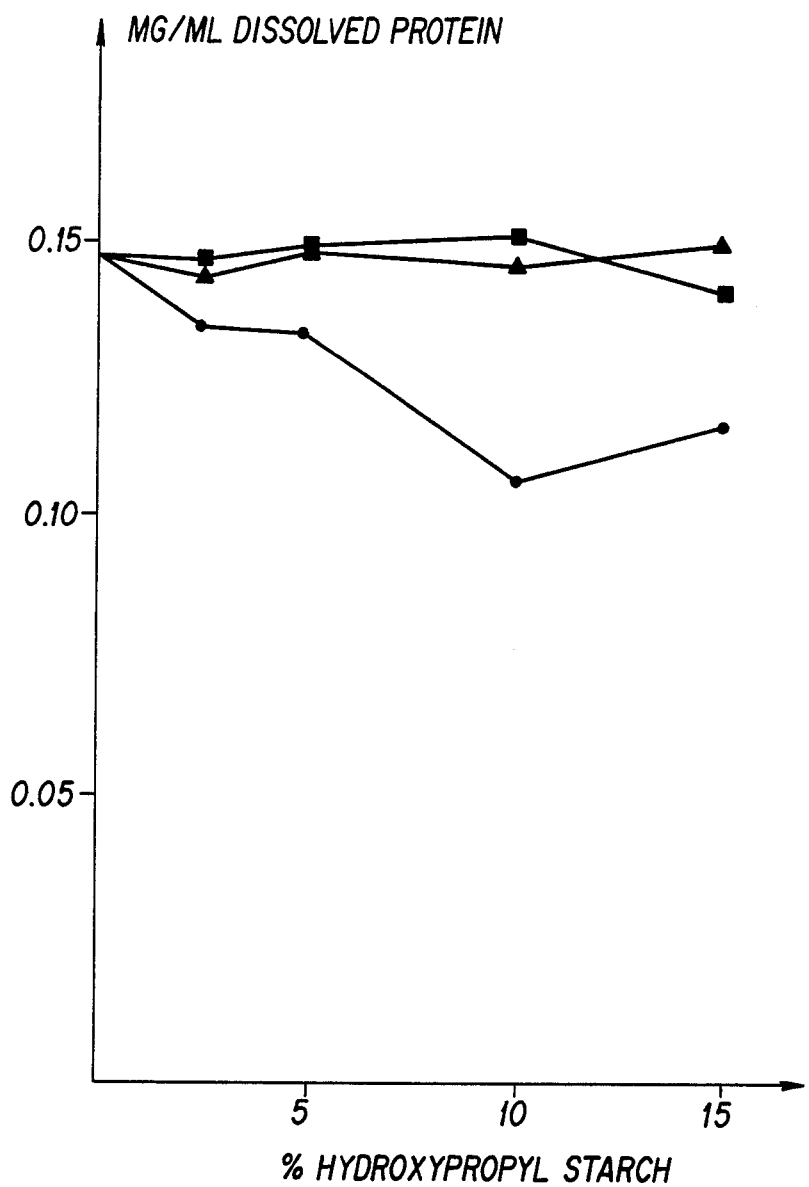
FIG. 2 shows the solubility of gammaglobuline in solutions of different bottom phase polymers.

In this case the gammaglobuline was not precipitated at any concentration of hydroxypropyl starch, which is shown in FIG. 2.

A comparison of the results according to Examples 18 and 19 shows that hydroxypropyl starch with an average molecular weight within the scope of the invention has no precipitating effect on gammaglobuline at an increasing polymer concentration. However, the precipitating effect is considerable at the use of hydroxypropyl starch with a molecular weight outside the scope of the invention.

EXAMPLE 20

In a beaker 0.9 g hydroxypropyl starch with a degree of substitution in respect of hydroxypropyl groups of 0.14 per glucose unit on an average and with an average molecular weight of 125000 was dissolved in 7.5 g 10 m M sodiumphosphate buffer at a pH of 7.0, together with 0.6 g polyethylene glycol with an average molecular weight of 20000 and 0.06 g of a substituted ligand consisting of Cibacron Blue—polyethylene glycol. The polyethylene glycol had the above molecular weight.

1 g of baker's yeast containing for instance the enzyme phosphofructokinase was added while stirring.

The stirring was continued for a short time. Then it was stopped, whereby the solution formed two phases. The bottom phase consisted of hydroxypropyl starch.

The result of the partition of the enzyme between the two phases is shown in Table 2.

EXAMPLE 21

The process according to Example 20 was repeated with the difference that dextran with an average molecular weight of 500000 was used instead of hydroxypropyl starch. The result of the partition of the enzyme between the two phases is shown in Table 2.

EXAMPLE 22

The process according to Example 20 was repeated with the difference that the enzyme glucose-6-phosphate dehydrogenase was used instead of extract from baker's yeast. The result of the partition of the enzyme between the two phases is shown in Table 2.

EXAMPLE 23

The process according to Example 22 was repeated with the difference that dextran with an average molecular weight of 500000 was used instead of hydroxypropyl starch. The result is shown in Table 2.

EXAMPLE 24

The process according to Example 20 was repeated with the difference that no substituted ligand was added. The result is shown in Table 2.

EXAMPLE 25

The process according to Example 21 was repeated with the difference that no substituted ligand was added. The result is shown in Table 2.

EXAMPLE 26

The process according to Example 22 was repeated with the difference that no substituted ligand was added. The result is shown in Table 2.

EXAMPLE 27

The process according to Example 23 was repeated with the difference that no substituted ligand was added. The result is shown in Table 2.

EXAMPLE 29

In a beaker 2.8 g hydroxypropyl starch with a degree of substitution in respect of hydroxypropyl grops of 0.14 per glucose unit on an average and with an average molecular weight of 125000 was dissolved in 20 ml water together with 1.0 g polyethylene glycol with an average molecular weight of 8000.

After stirring two phases were formed, of which the lower one consisted of hydroxypropyl starch. The viscosity of said phase was established by measuring the time needed for 5 ml solution to pass through a 10 ml pipette. The time was 21.6 seconds.

EXAMPLE 30

The process according to Example 29 was repeated with the difference that dextran with an average molecular weight of 500000 was used instead of the hydroxypropyl starch.

After stirring two phases were formed, of which the lower one consisted of dextran. The time needed for the passage through the pipette was measured to 37.5 seconds.

A comparison of the results according to Examples 29 and 30 shows that the hydroxypropyl starch according to the invention gave a considerably lower viscosity than dextran. This in turn means that the processing time in a twophase system with hydroxypropyl starch—polyethylene glycol gets shorter than in a twophase system with dextan—polyethylene glycol.

EXAMPLE 31

Enzymes were separated by a so-called counter-current distribution in twophase systems. As a buffer 0.25M sodium phosphate with a pH of 7.0 containing 5 m M $\beta$-mercaptoethanol, 0.1 m M EDTA and 0.02 m M $MgCl_2$ were used.

Examples 20–27 show that twophase systems consisting of HPS and PEG plus ligand work in the same way was twophase systems based on dextran and PEG plus ligand concerning purification of the enzymes phosphofructokinase and glucose-6-phosphate dehydrogenase. Then the enzymes are selectively distributed to the top phase when a ligand is present in the system.

EXAMPLE 28

0.7 g hydroxypropyl starch with a degree of substitution in respect of hydroxypropyl groups of 0.14 per glucose unit on an average and with an average molecular weight of 125000 was added to one beaker and dissolved in 10 m M sodium phosphate buffer at a pH of 7.0, together with 0.25 g polyethylene glycol with an average molecular weight of 8000. The total amount of twophase system was 5 g.

In a second beaker, twophase systems were mixed as disclosed above, with the difference that 0.5–2.5% of the polyethylene glycol consisted of a substituted ligand consisting of Cibacron Blue—polyethylene glycol, whereby the polyethylene glycol had the above-mentioned molecular weight. Moreover, 3% of the hydroxypropyl starch was replaced by a substituted ligand consisting of Procion Yellow—hydroxypropyl starch, whereby the hydroxypropyl starch had the above specification.

0.4 g of an extract of baker's yeast containing among other things the enzyme glucose-6-phosphate dehydrogenase was added while stirring. The stirring was continued for a short time and was then stopped, whereby two phases were formed. The top phase consisted of polyethylene glycol.

Figure 3:
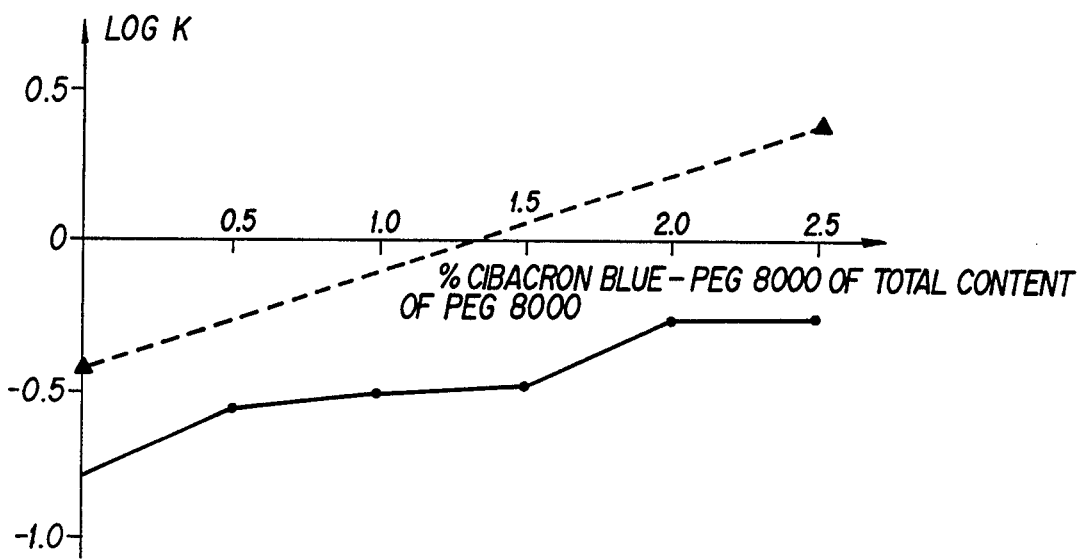
FIG. 3 shows the influence of polymer bonded ligands on the distribution of glucose-6-phosphate-dehydrosenase.

By addition of the ligand Cibacron Blue—polyethylene glycol the enzyme will be more and more distributed to the top phase. In a similar way the enzyme will be distributed to the bottom phase at the addition of Procion Yellow—hydroxypropyl starch. The result is shown in FIG. 3.

21 g hydroxypropyl starch with an average molecular weight of 125000 and a degree of substitution in respect of hydroxypropyl groups of 0.14 per glucose unit was dissolved in 53 g of the above-mentioned buffer. The buffer plus HPS make solution No. 1. 7.1 g polyethylene glycol with an average molecular weight of 20000 and 0.37 g of a substituted ligand, Cibacron Blue—polyethylene glycol were dissolved in 69 g of the above buffer. The buffer plus PEG plus ligand make solution No. 2. The polyethylene glycol had the above specification.

Solution No. 1 was distributed in 55 beakers with 0.87 ml in each. 1.13 ml of solution No. 2 and 0.27 g extract from baker's yeast containing the enzymes hexokinase, phosphofructokinase, 3-phosphoglycerate kinase, glucose-6-phosphate dehydrogenase, glyceraldehyde-3-phosphate dehydrogenase, enolase, phosphoglycerate mutase and alcohol dehydrogenase were added while stirring to the first three of the beakers.

When the stirring had been finished, two phases were formed, one of which consisted of hydroxypropyl starch and water. A first distribution of the enzymes took place. To improve said distribution, the top phase of the first beaker was transferred to the solution in the second beaker, whereupon 1.13 ml of solution No. 2 was added to the first beaker.

After another stirring, two phases were formed both in the first and in the second beaker. At the same time the enzymes were partitioned between the phases. The top phase in the second beaker was transferred to the solution in the third beaker. At the same time the top phase in the first beaker was transferred to the second beaker and another 1.13 ml of solution No. 2 was added to the first beaker.

The process was repeated until all 55 beakers contained two phases. In that way a separation of the enzymes was obtained, where enzymes with a strong distribution to the top phase were found in beakers with high ordinal numbers and enzymes with a strong distribution to the bottom phase were found in beakers with low ordinal numbers.

Figure 4:
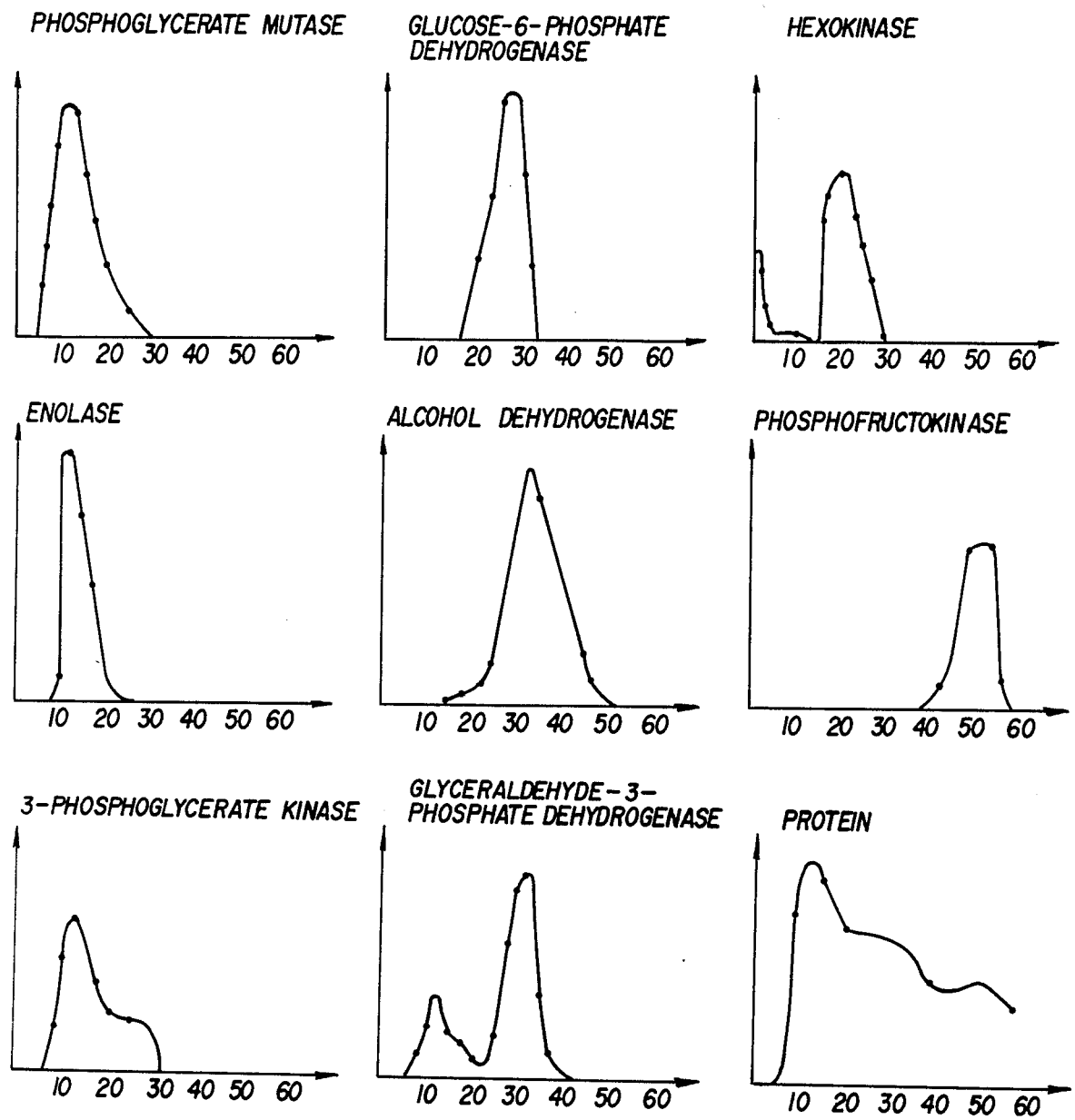
FIG. 4 shows enzyme activity as a function of breaker number.

The result is shown in FIG. 4.

EXAMPLE 32

In a beaker 14 g hydroxypropyl starch with a substitution degree in respect of hydroxypropyl groups of 0.14 per glucose unit on an average and with an average molecular weight of 125000 was dissolved in 81 g water together with 25 g polyethylene glycol with an average molecular weight of 8000.

After stirring two phases were formed.

The stability of the twophase system was controlled by storage in a refrigerator having a temperature of +4° C. No gel formation tendency could be observed after 14 days.

EXAMPLE 33

The process according to Example 32 was repeated with the difference that the hydroxypropyl starch had a degree of substitution in respect of hydroxypropyl groups of 0.01 per glucose unit and an average molecular weight of 14000.

A gel formation tendency could be observed after 3 days.

A comparison of the results according to Examples 32 and 33 shows that the degree of substitution in respect of hydroxypropyl groups influences the stability of the specific twophase systems.

The advantage of a twophase system being stable in cold is that certain biological materials need a processing in cold.

EXAMPLE 34

The ability of different starch derivatives to form twophase systems together with polyethylene glycol was tested. As shown in Table 3 only hydroxyalkyl derivatives of starch form functional twophase systems together with polyethylene glycol.

EXAMPLE 35

Deoxyribonucleic acid, DNA, and ribonucleic acid, RNA, were separated using a twophase countercurrent distribution system as disclosed in Example 31.

10 m M sodium phosphate buffer with a pH of 7.0 containing 0.1 m M sodium chloride was used as a buffer.

7.8 g hydroxypropyl starch with an average molecular weight of 125000 and with a degree of substitution in respect of hydroxypropyl groups of 0.14 per glucose unit on an average, was dissolved in 22.2 g of the buffer. This solution is called solution No. 1. 3.0 g polyethylene glycol with an average molecular weight of 8000 was dissolved in 27 g of the above buffer. This solution is called solution No. 2.

3 g of solution No. 1 was added to each of 10 testtubes. 3 g of solution No. 2 was added to testtube number one together with 5 mg DNA and 5 mg RNA. The testtube was shaken for a short time. two phases were formed when the shaking was stopped. The top phase was transferred to the solution in the second testtube. Then 3 g of solution No. 2 was added to the first testtube.

Figure 5:
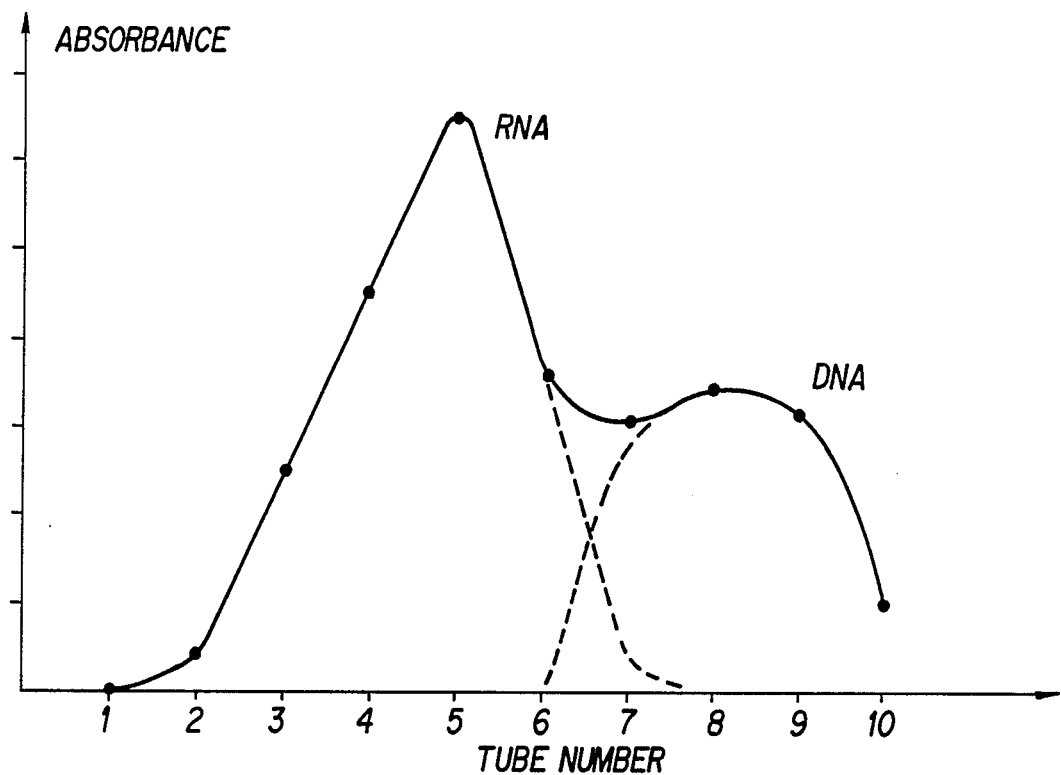
FIG. 5 shows countercurrent distribution of a mixture of DNA and RNA using a twophase system.

This process was continued in accordance with Example 31 but only with 10 testtubes. The result of the separation of DNA from RNA obtained is shown in FIG. 5.

EXAMPLE 36

In a beaker 0.65 g hydroxypropyl starch with an average molecular weight of 125000 and with a degree of substitution in respect of hydroxypropyl groups of 0.14 per glucose unit on an average, and 0.25 g polyethylene glycol with an average molecular weight of 8000, were dissolved in 10 m M sodium phosphate buffer with a pH of 7.0 to a total amount of 5 g.

10 mg of baker's yeast was added while stirring. The stirring was allowed to continue for a short time. When the stirring was stopped, two phases were formed.

The resulting distribution of the yeast cells is shown in Table 4.

EXAMPLE 37

The process according to Example 36 was repeated with the difference that the buffer contained 12.5 m M sodium chloride.

The resulting distribution of the yeast cells is shown in Table 4.

EXAMPLE 38

The process according to Example 36 was repeated with the difference that the buffer contained 25 m M sodium chloride. The resulting distribution of the yeast cells is shown in Table 4.

EXAMPLE 39

The process according to Example 36 was repeated with the difference that the buffer contained 50 m M sodium chloride. The resulting distribution of the yeast cells is shown in Table 4.

EXAMPLE 40

The process according to Example 36 was repeated with the difference that the buffer contained 75 m M sodium chloride. The resulting distribution of the yeast cells is shown in Table 4.

EXAMPLE 41

The process according to Example 36 was repeated with the difference that the buffer contained 100 m M sodium chloride. The resulting distribution of the yeast cells is shown in Table 4.

Examples 36–41 show that the partition of the yeast cells can be directed by varying the salt content. The result is shown in FIGS. 6a–d.

EXAMPLE 42

In a beaker 0.65 g hydroxypropyl starch with an average molecular weight of 125000 and with a degree of substitution in respect of hydroxypropyl groups of 0.14 per glucose unit on an average and 0.25 g polyethylene glycol with an average molecular weight of 8000, were dissolved in 10 m M sodium phosphate buffer with a pH of 7.0 containing 10 m M sodium chloride, to a total amount of 4.75 g.

0.25 g of synaptic membranes from calf brain was added while stirring. The stirring was continued for a short time. When the stirring was stopped, two phases were formed.

The resulting distribution of the membranes is shown in FIG. 7.

EXAMPLE 43

The process according to Example 42 was repeated with the difference that the buffer contained 25 m M sodium chloride.

The resulting distribution of the membranes is shown in FIG. 7.

EXAMPLE 44

The process according to Example 42 was repeated with the difference that the buffer contained 50 m M sodium chloride. The result of the distribution of the membranes is shown in FIG. 7.

EXAMPLE 45

The process according to Example 42 was repeated with the difference that the buffer contained 100 m M sodium chloride. The result of the distribution of the membranes is shown in FIG. 7.

Examples 42–45 show that the membranes can be directed from the top phase to the interface by an increased content of salt.

EXAMPLE 46

4000 g hydroxypropyl starch with an average molecular weight of 125000 and with a degree of substitution in respect of hydroxypropyl groups of 0.14 per glucose unit, 1520 g polyethylene glycol with an average molecular weight of 8000 and 4000 g muscle extract from pig containing lactate dehydrogenase (LDH) were dissolved in 40 m M sodium phosphate buffer with a pH of 7.9 to a total amount of 20000 g.

The mixture obtained was separated in two phases by using an Alfa-Laval separator LAPX 202. The amount of lactate dehydrogenase (LDH) in each phase was determined.

The result is shown in Table 5.

EXAMPLE 47

The process according to Example 46 was repeated with the difference that 1.5% of the polyethylene glycol had the ligand Procion Yellow bonded covalently. This ligand has affinity for LDH.

The result is shown in Table 5.

Examples 46–47 show that in a large scale the enzyme LDH can be extracted to the top phase by using a ligand attached to the polymer in the top phase.

The invention is not limited to the embodiments shown, since these can be modified in different ways within the scope of the invention.

TABLE 1
THE PARTITION COEFFICIENT'S DEPENDENCE OF THE MOLECULAR WEIGHT OF THE POLYMER IN THE TOP PHASE AND THE ION COMPOSITION OF THE SOLUTION

| Example | Twophase composition Bottom phase | Top phase | Buffer | Partition coefficient $K_f$ β-galaktosidase | Catalase |
|---|---|---|---|---|---|
| 2 | HPS | PEG 8000 | A | 23,2 | — |
| 3 | HPS | PEG 20.000 | A | 3,94 | — |
| 4 | HPS | PEG 8000 | B | 0,51 | — |
| 5 | HPS | PEG 20.000 | B | 0,16 | — |
| 6 | HPS | PEG 8000 | A | — | 1,50 |
| 7 | HPS | PEG 20.000 | A | — | 0,45 |
| 8 | HPS | PEG 8000 | B | — | 0,39 |
| 9 | HPS | PEG 20.000 | B | — | 0,16 |
| 10 | Dextran 500 | PEG 8000 | A | 1,59 | — |
| 11 | Dextran 500 | PEG 20.000 | A | 3 | — |
| 12 | Dextran 500 | PEG 8000 | B | 0,44 | — |
| 13 | Dextran 500 | PEG 20.000 | B | 0,2 | — |
| 14 | Dextran 500 | PEG 8000 | A | — | 0,78 |
| 15 | Dextran 500 | PEG 20.000 | A | — | 0,16 |
| 16 | Dextran 500 | PEG 8000 | B | — | 0,09 |
| 17 | Dextran 500 | PEG 20.000 | B | — | 0,2 |

Buffer A: 10 mM sodium phosphate buffer, pH 7.0
Buffer B: 10 mM sodium phosphate buffer, pH 7.0 and 0.1 M sodium chloride

TABLE 2
THE DISTRIBUTION COEFFICIENT'S DEPENDENCE OF A LIGAND, CIBACRON BLUE BONDED TO THE TOP PHASE POLYMER, POLYETHYLENE GLYCOL

| Example | Twophase composition Bottom phase | Top phase | Distribution coefficient, $K_f$ phosphofructo kinase | glucose-6-phosphate dehydrogenase |
|---|---|---|---|---|
| 20 | HPS | PEG 8000 + ligand | 3,5 | — |
| 21 | Dextran 500 | PEG 8000 + ligand | 10,0 | — |
| 22 | HPS | PEG 8000 + ligand | — | 2,4 |
| 23 | Dextran 500 | PEG 8000 + ligand | — | 0,42 |
| 24 | HPS | PEG 8000 | 0,14 | — |
| 25 | Dextran 500 | PEG 8000 | 0,06 | — |
| 26 | HPS | PEG 8000 | — | 0,37 |
| 27 | Dextran 500 | PEG 8000 | — | 0,10 |

TABLE 3
THE ABILITY OF DIFFERENT STARCH DERIVATIVES TO FORM TWOPHASE SYSTEMS WITH POLYETHYLENE GLYCOL

| Kind of derivative | Properties in a system with PEG |
|---|---|
| Nonionic: | |
| Dextrin, white | Retrograduates |
| Dextrin, yellow | High content necessary, coloured |
| Voxi maize (amylopectin) | Gel formation |
| Starch acetate | Retrograduates, salt necessary |
| Hydroxypropyl, acid hydrolized | Phase systems instable at + 4° C. |
| oxidized | Stable phase systems |
| Hydroxyethyl, oxidized | Phase systems instable at + 4° C. |
| Cationic: | |
| Quarternary ammonium | Precipitation |
| Cross-linked: | |
| Acetylated distarch phosphate | Precipitation |
| Hydroxypropyl distarch phosphate | Precipitation |

TABLE 4
The partition of yeast cells in a two-phase system with varying sodiumchloride concentration.

| | | Amount of yeast cells (%) | | |
|---|---|---|---|---|
| Example | NaCl (mM) | Top phase | Interface | Bottom phase |
| 36 | — | 97 | 3 | — |
| 37 | 12,5 | 89 | 11 | — |
| 38 | 25 | 20 | 80 | — |
| 39 | 50 | 0,8 | 97,8 | 1,4 |
| 40 | 75 | 0,5 | 61 | 38,5 |
| 41 | 100 | 0,4 | 33 | 66,6 |

TABLE 5
The partition of LDH in a large scale two-phase system using extract from pig muscle.

| Example | % ligand-PEG | % LDH in top phase | % LDH in bottom phase |
|---|---|---|---|
| 46 | — | 1 | 99 |
| 47 | 1,5 | 87 | 13 |

We claim:

1. A method for extraction, purification, and concentration comprising extracting, purifying, concentrating and/or separating by mixing at least one biological substance with,
   (A) hydroxyalkyl starch with a degree of substitution in respect of hydroxyalkyl groups of more than 0.02 per glucose unit on an average and with an average molecular weight lower than 800,000;
   (B) at least one polymer selected from the group consisting of polyethylene glycol, polypropylene glycol, methoxypolyethylene glycol, polyvinyl alcohol, polyvinyl pyrrolidone, hydroxyethyl cellulose, methyl cellulose, ethylhydroxyethyl cellulose, and a polymer of sucrose cross-linked with epichlorohydrin; and
   (C) an aqueous solution, allowing the mixture thus obtained to settle and to form two or more phases containing different components of the biological substance in separate phases, and recovering at least one of said components from the respective phase.

2. A method according to claim 1, wherein the mixing is obtained by stirring.

3. A method according to claim 1, characterized in that, in addition to the constituents (A), (B), and (C), at least one substituted ligand (D) is used.

4. A method according to claim 3, characterized in that the ligand (D) is substituted with or bonded to hydroxyalkyl starch and/or at least one polymer selected from the group consisting of polyethylene glycol, polypropylene glycol, methoxypolyethylene glycol, polyvinyl alcohol, polyvinyl pyrrolidone, methyl cellulose, ethylhydroxyethyl cellulose, hydroxyethyl cellulose, and a polymer of sucrose cross-linked with epichlorohydrin.

5. A method according to claim 1, wherein the hydroxyalkyl starch has an average molecular weight higher than 5000 and at most 250,000.

* * * * *